US00PP26410P3

(12) United States Plant Patent
Egger

(10) Patent No.: US PP26,410 P3
(45) Date of Patent: Feb. 9, 2016

(54) *AGASTACHE* PLANT NAMED 'KUDOS GOLD'

(50) Latin Name: ***Agastache* hybrid**
Varietal Denomination: Kudos Gold

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 132 days.

(21) Appl. No.: 14/120,308

(22) Filed: May 14, 2014

(65) Prior Publication Data

US 2015/0334904 P1 Nov. 19, 2015

(51) Int. Cl.
*A01H 5/02* (2006.01)

(52) U.S. Cl.
USPC ..... Plt./399

(58) Field of Classification Search
USPC ..... Plt./399
See application file for complete search history.

*Primary Examiner* — Anne Grunberg

(74) *Attorney, Agent, or Firm* — Klarquist Sparkman, LLP

(57) ABSTRACT

A new and distinct form of *Agastache* plant characterized by light yellow orange flowers in large inflorescences, a long bloom time, a short, compact habit, good winter hardiness, and excellent vigor.

1 Drawing Sheet

Botanical denomination: *Agastache* hybrid.
Variety designation: 'Kudos Gold'.

BACKGROUND OF THE INVENTION

The present invention relates to a new and distinct cultivar of *Agastache*, given the name, 'Kudos Gold'. *Agastache* is in the family Lamiaceae. This new variety is one of several selections of new *Agastache* using hardy and dwarf *Agastache* species in the breeding lines to provide hardiness and compactness. The new cultivar is a selection from the cross between the proprietary seedlings *Agastache* 101-3 (unpatented), as the seed parent, and *Agastache* 42-wt (unpatented), as the pollen parent. The new cultivar was selected for its compact habit, hardiness, and gold flowers in dense heads.

Compared to the seed parent, *Agastache* 101-3 the new cultivar is light yellow orange rather than yellow orange.

Compared to the pollen parent, *Agastache* 42-wt, the new cultivar is hardier and better branched with light yellow orange rather than white flowers.

Compared to *Agastache* 'Summer Glow', U.S. Plant Pat. No. 20,980, the new cultivar is hardier, shorter, and bushier with more intense light yellow orange flowers that do not fade.

This plant exhibits the following characteristics that make it unique:

1. light yellow orange flowers on numerous inflorescences,
2. a long bloom time,
3. a short, compact habit,
4. good winter hardiness, and
5. excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a six-month-old the new cultivar grown in a one gallon container in August in Canby, Oreg.

FIG. 2 shows one-year-old *Agastache* 'Kudos Gold' growing in the field in mid summer in Canby, Oreg.

DETAILED PLANT DESCRIPTION

The following is a detailed description of the new *Agastache* cultivar based on observations of 9-month-old specimens in early September growing in full sun in the field in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Upright.
*Type*.—Herbaceous perennial.
*Cold hardiness*.—USDA Zone 6-10.
*Size*.—Grows to 52 cm wide and 52 cm tall to the top of the flowers.
*Vigor*.—Excellent.
*Branching*.—About 12 main stems from the base, these branch at every node.
*Stem*.—Square in cross section, grows to 4 mm wide and 27 cm tall to the first flower, pubescent, internodes range from 2 cm to 5 cm long, Yellow Green 147B.
*Roots*.—White 155B, fibrous, plants root easily from stem tip cuttings.

Leaf:

*Type*.—Simple.

*Arrangement*.—Opposite.

*Shape*.—Ovate.

*Venation*.—Pinnate.

*Margins*.—Crenate.

*Apex*.—Acute.

*Base*.—Cordate to truncate.

*Blade size*.—Grows to 50 mm long and 35 mm wide.

*Surface texture*.—Pubescent on both sides.

*Petiole description*.—Grows to 25 mm long and 1 mm wide, pubescent, Yellow Green 147B.

*Leaf color*.—Top side Yellow Green 147A with vein 147C, bottom side closest to Yellow Green 147B with vein 147C.

*Fragrance*.—Aromatic.

Inflorescence:

*Type*.—Terminal spike with up to 11 whorls.

*Number of flowers*.—About 120 per spike.

*Size of inflorescence*.—Grows to 11.5 cm tall and 5 cm wide.

*Peduncle*.—Grows to 8 cm tall and 2 mm wide, pubescent, Yellow Green 147B.

*Pedicel*.—Grows to 1.5 mm long, pubescent, Yellow Green 147C.

*Bloom period*.—June through frost in Canby, Oreg.

Flower bud:

*Size*.—20 mm long and 4 mm wide at the widest point prior to opening.

*Description*.—Tubular.

*Surface texture*.—Pubescent.

*Color*.—Orange 26B.

Flower:

*Type*.—Zygomorphic.

*Shape*.—Bilabiate, tubular.

*Size*.—29 mm long and 7 mm wide.

*Corolla description*.—29 mm long and 7 mm wide; overall color both sides Yellow Orange 22B; glabrous inside and pubescent outside, tube 19 mm long and 1 mm to 3 mm wide; 2 upper lobes joined 4 mm long and 4 mm wide, each oblong, tips acute, margin entire; three lower lobes, two spreading sideways, each 3 mm long and 3 mm wide, tip acute, margin entire; bottom lobe cupped, broadly obovate, notched at the tip, margin irregularly serrate, 5.5 mm wide and 4 mm deep.

*Calyx description*.—Campanulate, 8 mm long and 2.5 mm wide, pubescent outside and glabrous inside, 5 lobed, lobes lanceolate, 2.5 mm long, margins entire, tips acuminate, Yellow Green 147C inside and outside on bottom 2/3 blending to Greyed Purple 186A on top 1/3.

*Pistil description*.—22 mm long, ovary 1 mm long, Yellow Green 145C, style 20 mm long, White NN155B blending to White N155C at top, stigma two-parted, 1 mm deep, White N155C.

*Stamen description*.—4 in number, paired and exerted, top two 16 mm long and bottom two 12 mm long, filaments White N155C, anthers 1 mm long, Greyed Purple 186D, pollen none.

*Fragrance*.—Aromatic.

*Lastingness*.—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as illustrated and described.

* * * * *

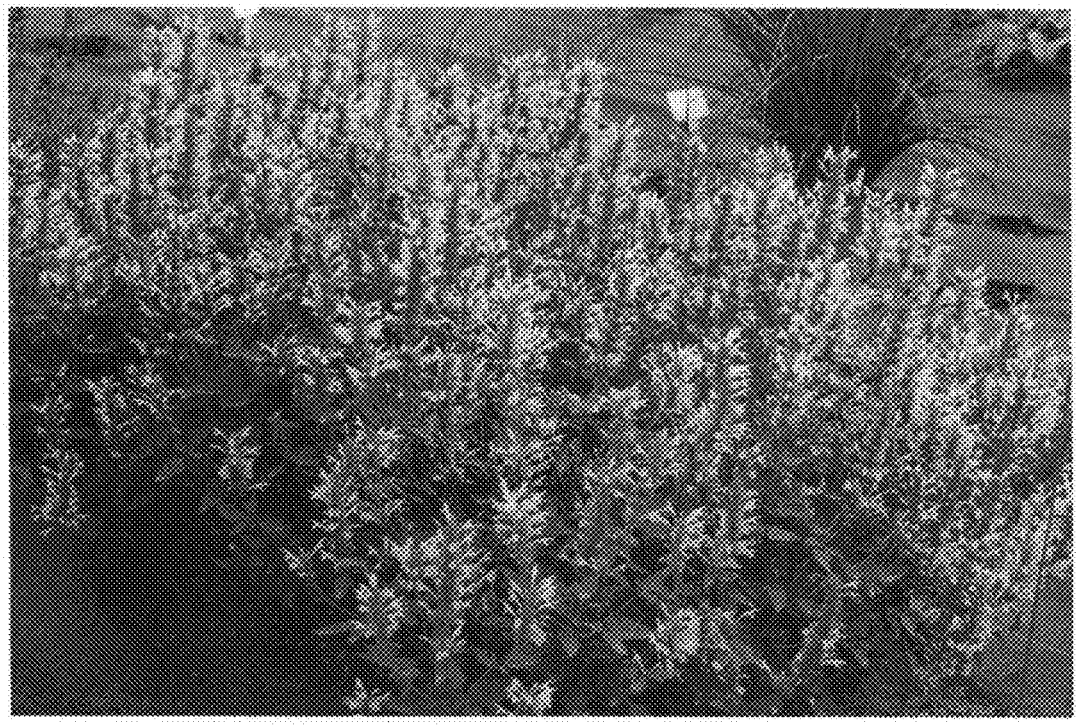

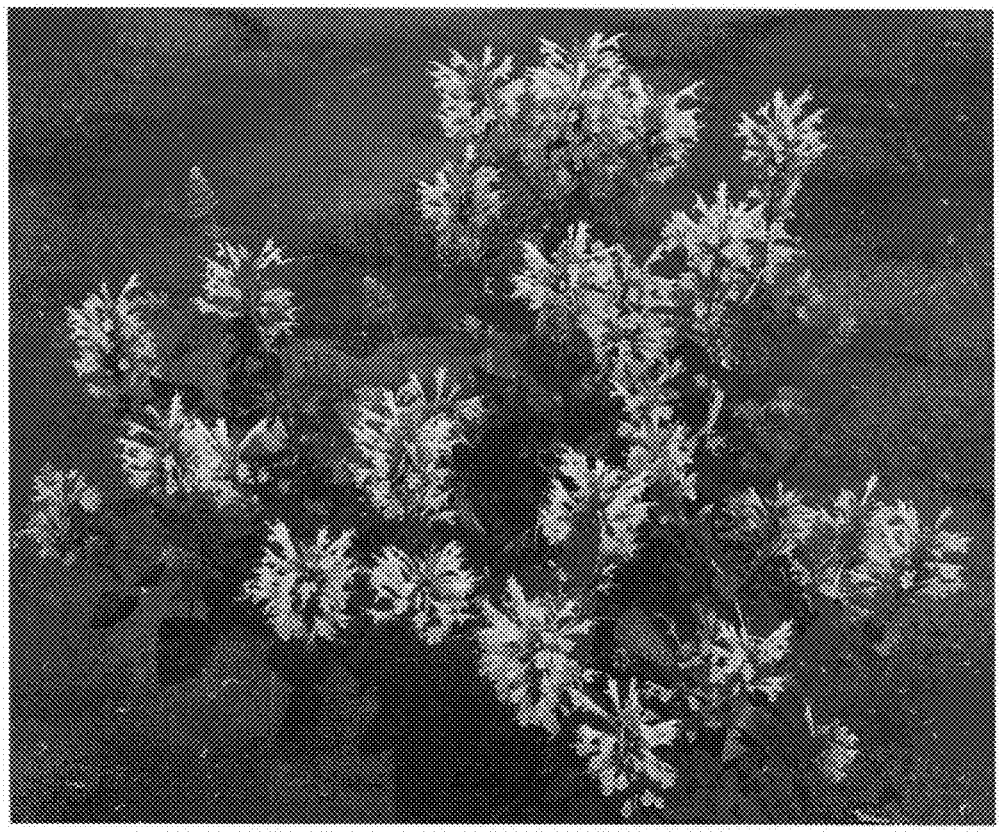
FIG. 1 above, FIG. 2 below